United States Patent
Katz et al.

(10) Patent No.: US 11,607,272 B2
(45) Date of Patent: Mar. 21, 2023

(54) VISUAL ROUTE INDICATION FOR ACTIVATION CLUSTERS

(71) Applicant: Biosense Webster (Israel) Ltd., Yokneam (IL)

(72) Inventors: Natan Sharon Katz, Atlit (IL); Benjamin Cohen, Haifa (IL); Lior Zar, Poria Illit (IL); Aharon Turgeman, Zichron Ya'acov (IL)

(73) Assignee: Biosense Webster (Israel) Ltd., Yokneam (IL)

(*) Notice: Subject to any disclaimer, the term of this patent is extended or adjusted under 35 U.S.C. 154(b) by 678 days.

(21) Appl. No.: 16/681,411

(22) Filed: Nov. 12, 2019

(65) Prior Publication Data
US 2021/0137600 A1    May 13, 2021

(51) Int. Cl.
*A61B 34/10*    (2016.01)
*A61B 18/14*    (2006.01)
*A61B 18/00*    (2006.01)

(52) U.S. Cl.
CPC ............. *A61B 34/10* (2016.02); *A61B 18/14* (2013.01); *A61B 2018/00982* (2013.01); *A61B 2034/105* (2016.02); *A61B 2034/107* (2016.02)

(58) Field of Classification Search
CPC .............. A61B 34/10; A61B 18/14; A61B 2018/00982; A61B 2034/105; A61B 2034/107
See application file for complete search history.

(56) References Cited

U.S. PATENT DOCUMENTS

| | | | |
|---|---|---|---|
| 5,833,621 A | 11/1998 | Panescu et al. | |
| 6,226,542 B1* | 5/2001 | Reisfeld | A61B 5/341 600/407 |
| 10,398,338 B2* | 9/2019 | Ghoraani | A61B 5/743 |
| 11,482,338 B2* | 10/2022 | Shamilov | G16H 20/30 |
| 2003/0023130 A1* | 1/2003 | Ciaccio | A61B 5/341 600/12 |
| 2004/0078036 A1* | 4/2004 | Keidar | A61B 34/20 606/41 |

(Continued)

OTHER PUBLICATIONS

Prathibhamol "Prediction of Cardiac Arrhythmia type using Clustering and Regression Approach (P-CA-CRA)", IEEE 2017 (Year: 2017).*

(Continued)

*Primary Examiner* — Oommen Jacob
(74) *Attorney, Agent, or Firm* — Volpe Koenig (57) ABSTRACT

Methods, apparatus, and systems for medical procedures are disclosed herein and include receiving a first electrical activity at a first time for a plurality of points on an intrabody surface. A first cluster of points is identified from the plurality of points, based on the first electrical activity, the first cluster of points each exhibiting electrical activity above an activity threshold. A second electrical activity is received at a second time for the plurality of points on the intra-body surface. A second cluster of points is identified from the plurality of points, based on the second electrical activity. The first cluster of points and the second cluster of points are determined to be related based on a propagation threshold. A first visual indication for a first propagation route is provided from the first cluster of points to the second cluster of points.

18 Claims, 7 Drawing Sheets

(56) References Cited

U.S. PATENT DOCUMENTS

| | | | |
|---|---|---|---|
| 2004/0243012 A1* | 12/2004 | Ciaccio | A61B 18/1492 600/512 |
| 2008/0081990 A1 | 4/2008 | Berenfeld et al. | |
| 2009/0299424 A1* | 12/2009 | Narayan | A61N 1/36592 607/9 |
| 2012/0157822 A1* | 6/2012 | van Dam | A61B 5/318 600/513 |
| 2013/0274582 A1* | 10/2013 | Afonso | A61B 5/065 600/374 |
| 2015/0065836 A1* | 3/2015 | Thakur | A61B 5/367 600/374 |
| 2015/0164356 A1* | 6/2015 | Merschon | A61B 5/318 600/374 |
| 2015/0208942 A1* | 7/2015 | Bar-Tal | A61B 34/20 600/509 |
| 2015/0327805 A1* | 11/2015 | Ben-Haim | A61B 6/032 600/431 |
| 2016/0095531 A1 | 4/2016 | Narayan et al. | |
| 2016/0106376 A1* | 4/2016 | Li | A61B 5/6852 600/373 |
| 2017/0086694 A1* | 3/2017 | Stewart | A61B 5/349 |
| 2017/0281031 A1* | 10/2017 | Houben | A61B 18/12 |
| 2017/0303807 A1 | 10/2017 | Laughner et al. | |
| 2018/0279895 A1 | 10/2018 | Relan | |
| 2018/0279896 A1 | 10/2018 | Ruppersberg | |
| 2019/0104962 A1* | 4/2019 | Ghoraani | A61B 5/7282 |
| 2019/0216347 A1 | 7/2019 | Ghodrati | |
| 2020/0367751 A1* | 11/2020 | Vandersickel | A61B 5/316 |
| 2021/0137600 A1* | 5/2021 | Katz | A61B 5/287 |

OTHER PUBLICATIONS

Alcaine "Estimation of High-Density Activation Maps During Atrial Fibrillation", Computing in Cardiology 2015; 42:825-828. (Year: 2015).*

European Search Report for corresponding EPA No. 20206965.4 dated Mar. 15, 2021.

Zhang Yongjie et al., "An atlas-based geometry pipeline for cardia Hermite model construction and diffusion tensor reorientation", Medical Image Analysis, vol. 16, No. 6, Aug. 1, 2012, pp. 1130-1141.

Alejandro F. Frangi et al., "Three-Dimensional Modeling for Functional Analysis of Cardiac Images: A Review", IEEE Transactions on Medical Imaging, vol. 20, No. 1, Jan. 1, 2001.

* cited by examiner

VISUAL ROUTE INDICATION FOR ACTIVATION CLUSTERS

FIELD OF INVENTION

The present application provides systems, apparatuses, and methods for improving intra-body visualization.

BACKGROUND

Medical conditions such as cardiac arrhythmia (e.g., atrial fibrillation (AF)) are often diagnosed and treated via intra-body procedures. For example, electrical pulmonary vein isolation (PVI) from the left atrial (LA) body is performed using ablation for treating AF. Pulmonary vein isolation, and many other minimally invasive catheterizations, require real-time visualization and mapping of an intra-body surface.

Visualization and mapping of intra-body signals and/or body parts can be performed by mapping propagation of activation waves. Fluoroscopies, computerized tomography (CT) and magnetic resonance imaging (MRI), as well as other techniques may require a greater than desirable amount of time or resources to provide the visualization and mapping.

Traditionally, a medical professional may manually identify electrical activity based on visually observing changes in the electrical activity. However, such manual identification may be time consuming and/or otherwise inefficient.

SUMMARY

Methods, apparatus, and systems for medical procedures are disclosed herein and include receiving a first electrical activity at a first time for a plurality of points on an intrabody surface. A first cluster of points is identified from the plurality of points, based on the first electrical activity, the first cluster of points each exhibiting electrical activity above an activity threshold. A second electrical activity is received at a second time for the plurality of points on the intra-body surface. A second cluster of points is identified from the plurality of points, based on the second electrical activity. The first cluster of points and the second cluster of points are determined to be related based on a propagation threshold. A first visual indication for a first propagation route is provided from the first cluster of points to the second cluster of points.

BRIEF DESCRIPTION OF THE DRAWINGS

A more detailed understanding can be had from the following description, given by way of example in conjunction with the accompanying drawings wherein.

DETAILED DESCRIPTION

According to exemplary embodiments of the present invention, electrical propagation across an intra-body organ (e.g., a heart) may be sensed and propagation routes based on the electrical activity may be visually displayed. The electrical activity may be sensed for clusters of points at different times, based on techniques disclosed herein. The propagation routes for electrical activity based on one or more clusters of points may be determined based on attributes such as elapsed time and propagation velocity of electrical activity.

A cluster of points may be determined based on electrical activation of a plurality of points that are within a threshold proximity relative to each other. The threshold proximity may be, for example, 3 mm or, more generally, may be in the single digit millimeter range. For example, a first cluster of points may be determined based on a plurality of points exhibiting electrical activity above an activity threshold. The points in the first cluster of points may each be within a threshold proximity of at least one other electrically active point such that any outlier point that is greater than the threshold proximity from each of the other activated points is not part of the first cluster of points. Notably, the threshold proximity, as applied herein, may not be a predetermined area of an intra-body organ but, rather, may be a distance applied to each electrically activated point on the intra-body organ, at a given time, in order to determine the location of one or more clusters of points.

The electrical propagation of clusters of points may be determined based on the movement, within an intra-body organ, of the electrical activity after a given amount of elapsed time. The electrical propagation of clusters of points may be visually provided by, for example, arrows overlaid on a rendering of an intra-body organ which extend from a given cluster of points at a first time to the given cluster of points at a second time. A cluster of points may propagate along a route for a period of time, may split into two or more clusters of points, or may dissipate after a period of time.

The techniques provided herein may enable the visual representation of electrical propagation of clusters of points such that electrical points on an intra-body organ are automatically clustered and such that their electrical propagation is automatically identified and visually represented for efficient medical analysis and use. Such visual representation may enable a more efficient understanding of the electrical activity of an intra-body organ and may expedite analysis and procedure times.

Figure 1:
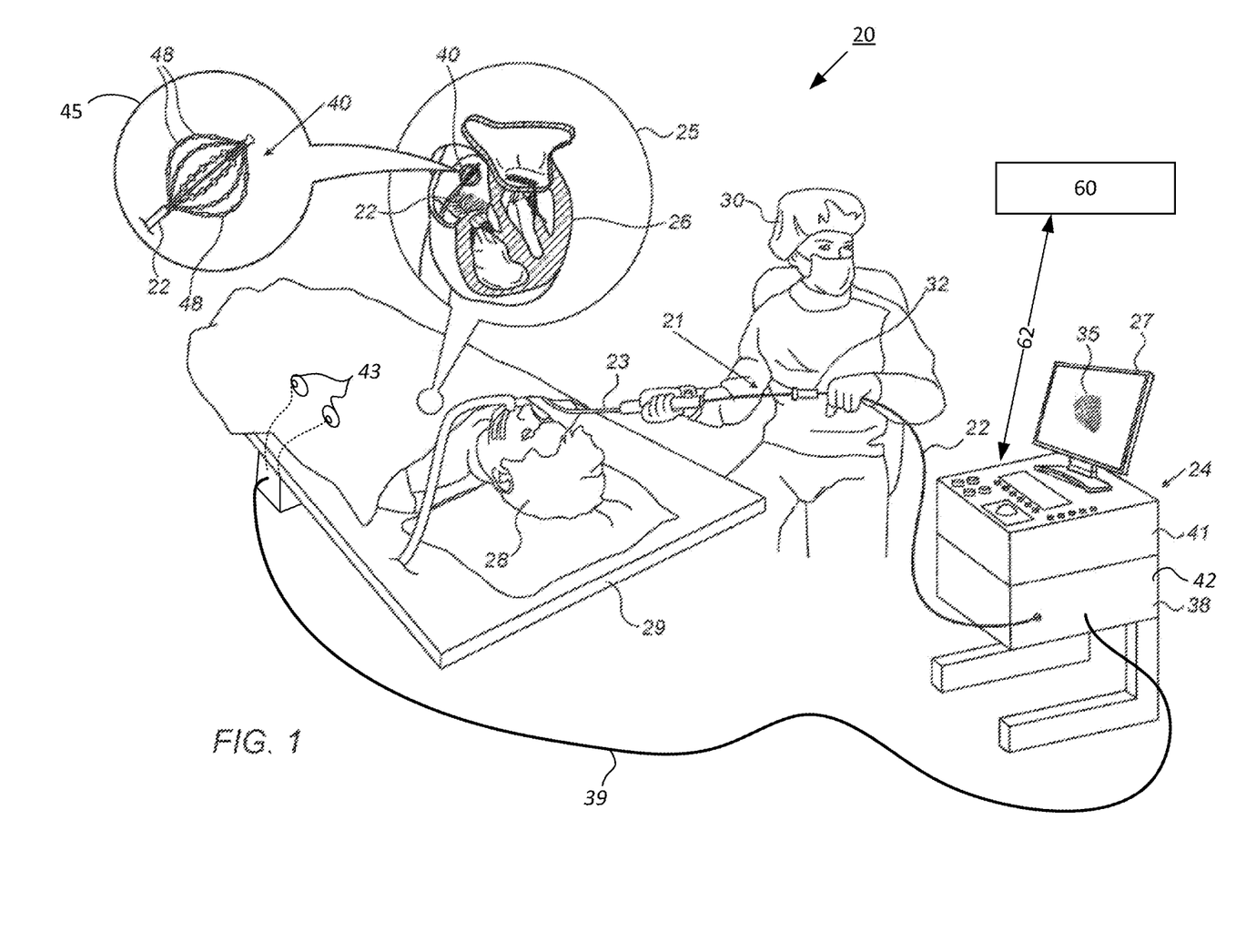
FIG. 1 is a diagram of an exemplary system in which one or more features of the disclosure subject matter can be implemented.

FIG. 1 is a diagram of an exemplary mapping system 20 in which one or more features of the disclosure subject matter can be implemented. Mapping system 20 may include a device, such as a catheter 40, that is configured to obtain electrical activity data in accordance with an exemplary embodiment of the present invention. Although catheter 40 is shown to have a basket shape, it will be understood that a catheter of any shape that includes one or more elements (e.g., electrodes) may be used to implement the exemplary embodiments disclosed herein. Mapping system 20 includes a probe 21, having a shaft 22 that may be navigated by a medical professional 30 into a body part, such as heart 26, of a patient 28 lying on a table 29. As shown in FIG. 1, medical professional 30 may insert shaft 22 through a sheath 23, while manipulating the distal end of shaft 22 using a manipulator 32 near the proximal end of the catheter and/or deflection from the sheath 23. As shown in an inset 25, catheter 40 may be fitted at the distal end of shaft 22. Catheter 40 may be inserted through sheath 23 in a collapsed state and may be then expanded within heart 26.

According to an exemplary embodiment of the present invention, the catheter 40 may be configured to obtain electrical activity within a cardiac chamber of the heart 26. Inset 45 shows catheter 40 in an enlarged view, inside a cardiac chamber of heart 26. As shown, catheter 40 may include an array of elements (e.g., electrodes 48) coupled onto splines that form the shape of the catheter 40. The elements (e.g., electrodes 48) may be any elements configured to obtain biometric data and may be electrodes, transducers, or one or more other elements. It will be understood that although one catheter 40 is shown, multiple catheters may be used to collect electrical activity of an intra-body organ.

According to exemplary embodiments disclosed herein, electrical activity may be any applicable electrical signals that may be measured based on one or more thresholds and may be sensed and/or augmented based on signal to noise ratios and/or other filters. A catheter, such as catheter 40 may also be configured to sense additional biometric data in addition to electrical activity. The additional biometric data may include one or more of local activation times (LATs), topology, bipolar mapping, dominant frequency, impedance, or the like. Local activation times may be points in time of a threshold activity corresponding to a local activation, calculated based on a normalized initial starting point. A topology may correspond to the physical structure of a body part or a portion of a body part and may correspond to changes in the physical structure relative to different parts of the body part or relative to different body parts. A dominant frequency may be a frequency or a range of frequencies that is prevalent at a portion of a body part and may be different in different portions of the same body part. For example, the dominant frequency of a pulmonary vein of a heart may be different than the dominant frequency of the right atrium of the same heart. Impedance may be the resistance measurement at a given area of a body part and may be calculated as a standalone value, based on a frequency, and/or in combination with additional considerations such as blood concentration.

As shown in FIG. 1, the probe 21 and catheter 40 may be connected to a console 24. Console 24 may include a processor 41, such as a general-purpose computer, with suitable front end and interface circuits 38 for transmitting and receiving signals to and from catheter 40, as well as for controlling the other components of mapping system 20. In some exemplary embodiments of the present invention, processor 41 may be further configured to receive electrical activity data, allocate clusters of points at different times and provide a visual indication from a first cluster of points to a related second cluster of points. According to exemplary embodiments of the present invention, rendering data may be used to provide the medical professional 30 with a rendering of one or more body parts on a display 27, e.g., a body part rendering 35. According to an exemplary embodiment of the present invention, the processor may be external to the console 24 and may be located, for example, in the catheter, in an external device, in a mobile device, in a cloud-based device, or may be a standalone processor.

As noted above, processor 41 may include a general-purpose computer, which may be programmed in software to carry out the functions described herein. The software may be downloaded to the general-purpose computer in electronic form, over a network, for example, or it may, alternatively or additionally, be provided and/or stored on non-transitory tangible media, such as magnetic, optical, or electronic memory. The exemplary configuration shown in FIG. 1 may be modified to implement the embodiments disclosed herein. The disclosed exemplary embodiments may similarly be applied using other system components and settings. Additionally, mapping system 20 may include additional components, such as elements for sensing biometric patient data, wired or wireless connectors, processing and display devices, or the like.

According to an exemplary embodiment of the present invention, a display connected to a processor (e.g., processor 41) may be located at a remote location such as a separate hospital or in separate healthcare provider networks. Additionally, the mapping system 20 may be part of a surgical system that is configured to obtain anatomical and electrical measurements of a patient's organ, such as a heart, and performing a cardiac ablation procedure. An example of such a surgical system is the Carto® system sold by Biosense Webster.

The mapping system 20 may also, and optionally, obtain biometric data such as anatomical measurements of the patient's heart using ultrasound, computed tomography (CT), magnetic resonance imaging (MRI) or other medical imaging techniques known in the art. The mapping system 20 may obtain electrical measurements using catheters, electrocardiograms (EKGs) or other sensors that measure electrical properties of the heart. The biometric data including anatomical and electrical measurements may then be stored in a local memory 42 of the mapping system 20, as shown in FIG. 1. Notably, memory 42 may store biometric data for multiple different modalities at the same time. The biometric data may be transmitted to the processor 41 from the memory 42. Alternatively, or in addition, the biometric data may be transmitted to a server 60, which may be local or remote, using a network 62.

Network 62 may be any network or system generally known in the art such as an intranet, a local area network (LAN), a wide area network (WAN), a metropolitan area network (MAN), a direct connection or series of connections, a cellular telephone network, or any other network or medium capable of facilitating communication between the mapping system 20 and the server 60. The network 62 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 62.

In some instances, the server 60 may be implemented as a physical server. In other instances, server 60 may be implemented as a virtual server a public cloud computing provider (e.g., Amazon Web Services (AWS) @).

Control console 24 may be connected, by a cable 39, to body surface electrodes 43, which may include adhesive skin patches that are affixed to the patient 28. The processor, in conjunction with a current tracking module, may determine position coordinates of the catheter 40 inside the body part (e.g., heart 26) of a patient. The position coordinates may be based on impedances or electromagnetic fields measured between the electrodes 43 and the electrodes 48 or other electromagnetic components of the catheter 40.

Processor 41 may comprise real-time noise reduction circuitry typically configured as a field programmable gate array (FPGA), followed by an analog-to-digital (A/D) ECG (electrocardiograph) or EMG (electromyogram) signal conversion integrated circuit. The processor 41 may pass the signal from an A/D ECG or EMG circuit to another processor and/or can be programmed to perform one or more functions disclosed herein.

Control console 24 may also include an input/output (I/O) communications interface that enables the control console to transfer signals from, and/or transfer signals to electrodes 48 and electrodes 43. Based on signals received from electrodes 48 and/or electrodes 43, processor 41 may generate rendering data that enables a display, such as display 27 to render a body part, such as a body part rendering 35 and biometric data of multiple modalities as part of the body part rendering 35.

During a procedure, processor 41 may facilitate the presentation of a body part rendering 35, including one or more clusters of points that are active at a given time. The processor 41 may identify the one or more clusters at the given time as well as one or more other related or unrelated clusters at a subsequent times. The processor 41 may also determine a propagation route based on the two or more related clusters of points and provide a visual indication of the propagation route accordingly. The electrical activity may be stored in a memory 42 and the processor 41 may have access to the electrical activity stored in memory 42 to determine the clusters of point and the corresponding propagation route(s). The propagation route(s) may be provided to a medical professional 30 on a display 27.

Memory 42 may comprise any suitable volatile and/or non-volatile memory, such as random-access memory or a hard disk drive. In some exemplary embodiments of the present invention, medical professional 30 may be able to manipulate a body part rendering 35 using one or more input devices such as a touch pad, a mouse, a keyboard, a gesture recognition apparatus, or the like. In alternative exemplary embodiments of the present invention, display 27 may include a touchscreen that can be configured to accept inputs from medical professional 30, in addition to presenting a body part rendering 35, including the propagation route(s).

Figure 2:
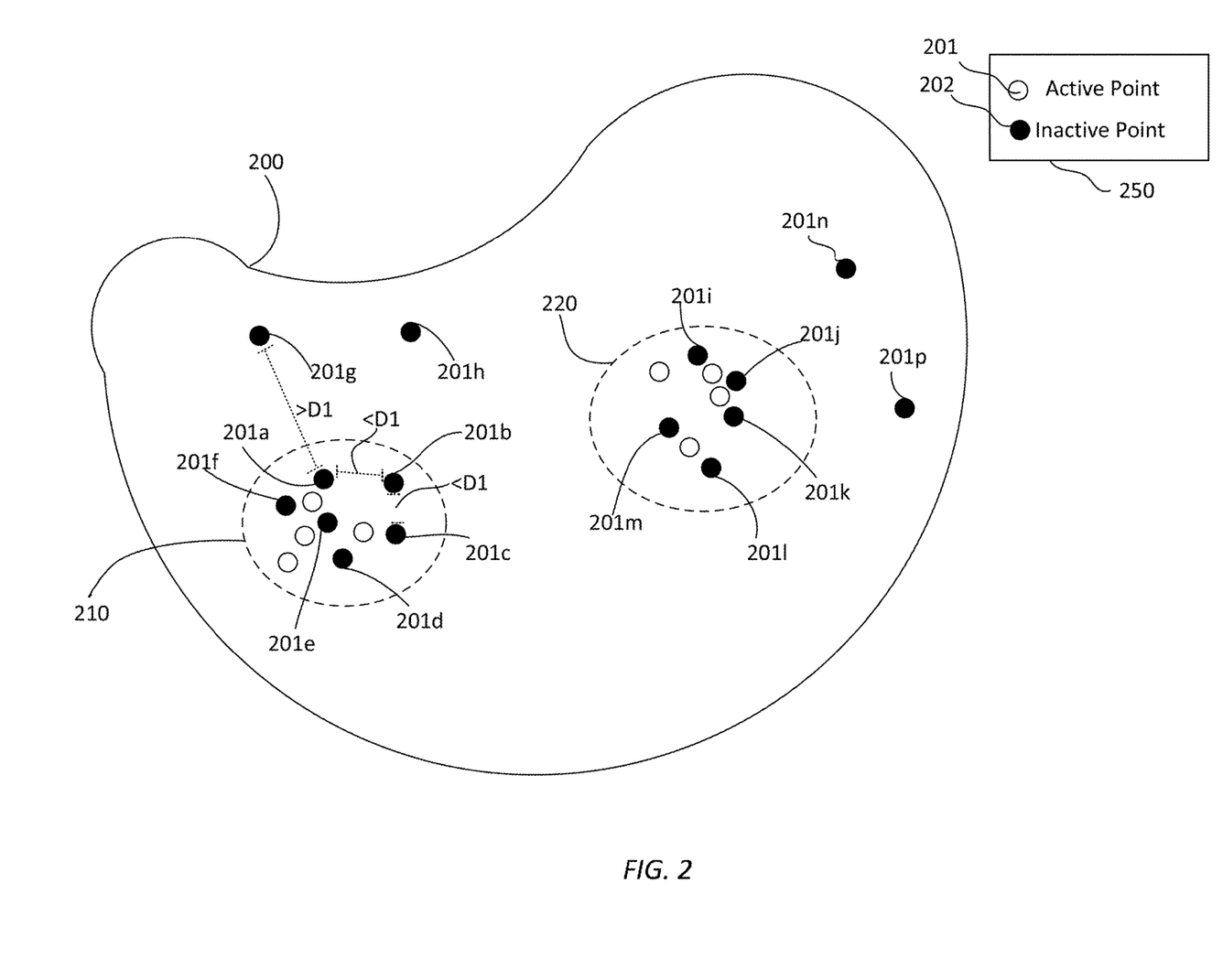
FIG. 2 is a diagram for determining clusters of points of an intrabody organ.

FIG. 2 shows the surface of an intra-body chamber 200 (e.g., a heart chamber) that includes a plurality of active points 201 and inactive points 202, as indicated by legend 250, at a first time. Each of the active points 201 and inactive points 202 may be points on the surface of the intra-body chamber 200 where an EGM signal is sensed. The EGM signal may be sensed by a catheter, such as catheter 40 of FIG. 1, and more specifically by an electrode, such as electrodes 48 of FIG. 1, on a catheter. The active points 201 correspond to points on the intra-body chamber 200 that have an EGM signal voltage greater than an activity threshold. The inactive points 202 correspond to points on the intra-body chamber 200 that have an EGM signal voltage below an activity threshold. The activity threshold may be, for example, 0.05 mV such that an EGM signal voltage greater than or equal to 0.05 mV corresponds to an active point 201 and a EGM signal voltage less than 0.05 mV corresponds to an inactive point 202. The activity threshold may be pre-determined or may be dynamically determined based on an analysis of the EGM signals from a plurality of the points on the intra-body chamber 200. The EGM signal voltages at points on the intra-body chamber 200 may be compared to an activity threshold after applying one or more applicable filters such as a signal-to-noise based filter, high pass filter, low pass filter, or the like.

As shown in FIG. 2, one or more clusters of points may be determined based on the relative distances between active points 201. A first cluster of points 210 may be determined based on each of the active points 201a-201f being within a threshold proximity D1 (i.e., <D1) from each other. As an example, D1 may be 3 mm. An example of an active point being within the threshold proximity D1 from another point is shown between active points 201a and 201b where the distance between active points 201a and 201b is <D1. Another example of an active point being within the threshold proximity D1 from another point is shown between active points 201b and 201c where the distance between active points 201b and 201c is <D1. It will be noted that although clusters of points (e.g., cluster of points 210) is shown as a boundary (e.g., the dashed circle of FIG. 2 that indicates the cluster of points 210), a cluster of points is a set of points and not a pre-defined shape. Accordingly, although a cluster of points may be referred to herein as a number of active points within a shape (e.g., a circle), such reference is only provided for simplicity.

Outlier active points 201g and 201h may a distance greater than the threshold proximity D1 from each of the active points 201a-201f and, accordingly, may not be part of the first cluster of points 210. FIG. 2 shows an example distance greater than D1 between outlier active point 201g and the closest active point 201a within the first cluster of points 210.

Similarly, a second cluster of points 220, as shown in FIG. 2, may be determined based on each of the active points 201i-201m being within the threshold proximity D1 (i.e., <D1) from each other. Outlier active points 201n and 201p may be at a distance greater than the threshold proximity D1 from each of the active points 201i-201m and, accordingly, may not be part of the second cluster of points 220.

According to an exemplary embodiment of the present invention, one or more clusters of points may be determined using a density-based spatial clustering of applications with noise (DBSCAN) algorithm. The DBSCAN algorithm is a density-based clustering non-parametric algorithm such that given a set of points in a space (e.g., intra-body chamber), points that are closely spaced together (e.g., points with a plurality of nearby neighboring points within a threshold proximity) are grouped as a cluster of points. Outlier points that lie alone in low-density regions (i.e., whose nearest neighbors are too far away) are not included in the cluster of points.

According to exemplary embodiments of the present invention, outlier points such as outlier active points 201g, 201h, 201n, and 201p may be grouped as a separate cluster of points if they are within the threshold proximity D1 from each other.

Figure 3:
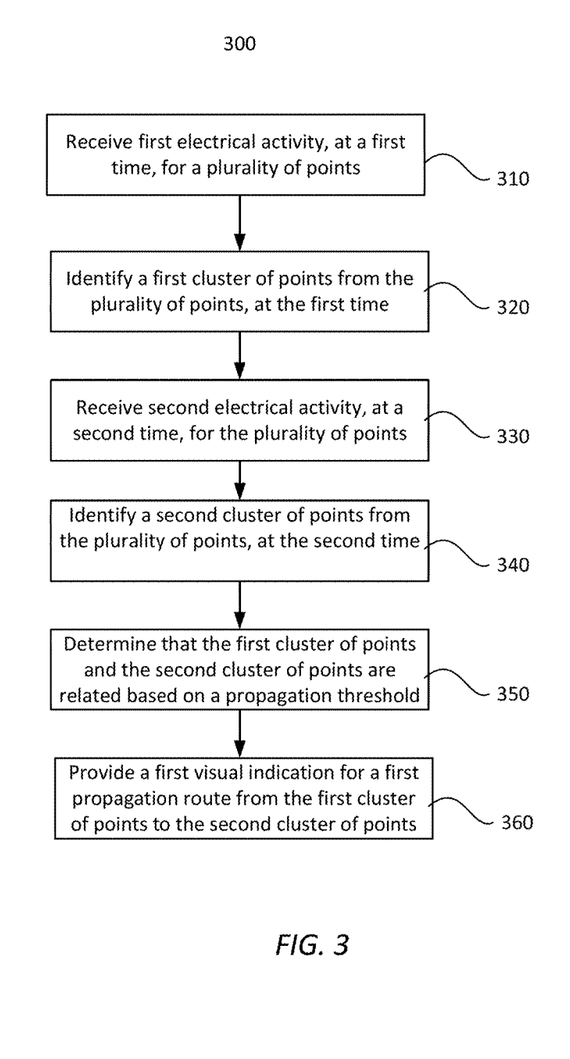
FIG. 3 is a flowchart for providing a visual indication of a propagation route.

FIG. 3 shows a process flowchart 300 for providing a visual indication from a first cluster of points at a first time to a second cluster of related points at a second time.

At step 310 of the process illustrated in FIG. 3, first electrical activity for a plurality of points on an intra-body surface, at a first time, may be received. The first electrical activity may be received by EGM signals collected using one or more catheters (e.g., catheter 40 of FIG. 1) including one or more electrodes (e.g., electrode 48 of FIG. 1). The electrical activity may be amplitudes of voltage passing through the plurality of active points at the first time. The first electrical activity at the first time for the plurality of points may be stored in a memory (e.g., memory 42 of FIG. 1) and may be received by a processor (e.g., processor 41).

At step 320 of the process illustrated in FIG. 3, a first cluster of points may be identified from the plurality of points in accordance with the techniques described herein including those in reference to FIG. 2. The first cluster of points may each exhibit electrical activity above an activity threshold. For example, a first cluster of points may be identified such that each of the points within the first cluster of points that exhibit electrical activity over the activity threshold are within a proximity threshold (e.g., D1 of FIG. 2) of at least one other point in the first cluster of points. Outlier points (e.g., outlier points 201g, 201h, 201n, and 201p of FIG. 2) that are greater than the proximity threshold from each of the points determined to be in the first cluster may not be included in the first cluster of points. It will be understood that although a first cluster of points at a first time is identified in reference to the process illustrated in FIG. 3, a plurality of clusters of points may be identified at the first time, as further disclosed herein.

At step 330 of the process illustrated in FIG. 3, second electrical activity for a plurality of points on an intra-body surface, at a second time, may be received. The second electrical activity for the plurality of points at the second time may be received for the same plurality of points as those that exhibited electrical activity at step 310 or may be different than (e.g., a subset of, overlapping with, or completely different than) the plurality of points at step 330 of FIG. 3. The second electrical activity may be received by EGM signals collected using one or more catheters (e.g., catheter 40 of FIG. 1) including one or more electrodes (e.g., electrode 48 of FIG. 1). The electrical activity may be amplitudes of voltage passing through the plurality of points at the second time. The second electrical activity at the second time for the plurality of points may be stored in a memory (e.g., memory 42 of FIG. 1) and may be received by a processor (e.g., processor 41).

At step 340 of the process illustrated in FIG. 3, a second cluster of points may be identified from the plurality of points, based on the second electrical activity, in accordance with the techniques described herein including those in reference to FIG. 2. The second cluster of points may each exhibit electrical activity above an activity threshold. For example, a second cluster of points may be identified such that each of the points within the second cluster of points that exhibit electrical activity over the activity threshold are within a threshold proximity (e.g., D1 of FIG. 2) of at least one other point in the second cluster of points. Outlier points (e.g., outlier points 201g, 201h, 201n, and 201p of FIG. 2) that are greater than the threshold proximity from each of the points determined to be in the second cluster may not be included in the second cluster of points. It will be understood that although a second cluster of points at a second time is identified in reference to the process illustrated in FIG. 3, a plurality of clusters of points may be identified at the second time, as further disclosed herein.

At step 350 of the process illustrated in FIG. 3, a determination may be made that the first cluster of points and the second cluster of points are related, based on a propagation threshold. The propagation threshold may be a distance determined based on a propagation velocity and a duration of time (i.e., the second time subtracted from the first time).

Accordingly, the determination that the first cluster of points and the second cluster of points are related may be made based on whether the second cluster of points is within a propagation threshold distance from the first cluster of points. For example, if the propagation velocity is 2 µm/millisecond and the difference between the second time and the first time is 3 milliseconds, then the propagation velocity (i.e., 2 µm/millisecond) multiplied by the duration of time (i.e., 3 milliseconds) results in a propagation threshold of 6 µm.

According to an exemplary embodiment of the present invention, a propagation velocity and, accordingly, corresponding propagation thresholds, may be pre-determined. A pre-determined propagation velocity may be stored, for example, in memory (e.g., memory 42 of FIG. 1) and may be accessible to a processor (e.g., processor 41 of FIG. 1). The processor (e.g., processor 41) may multiply the pre-determined stored prorogation velocity by a difference in time to determine prorogation thresholds applicable to two or more clusters of points at two or more times.

According to another exemplary embodiment of the present invention, a propagation velocity and, accordingly, corresponding propagation thresholds, may be dynamically determined. A dynamically determined prorogation velocity may be based on any number of applicable factors such as, but not limited to, tissue thickness, a specific intra-body organ (e.g., a heart), a specific portion of an intra-body organ (e.g., a heart chamber or vein), a medical condition, a patient characteristic, or the like. For example, a processor (e.g., processor 41 of FIG. 1) may receive and/or access one or more variables (e.g., tissue thickness, specific intra-body organ, etc.) and may determine a propagation velocity based on the one or more variables.

According to other exemplary embodiments of the present invention, a propagation threshold may be determined based on factors other than or in combination with a propagation velocity. Such factors may include, but are not limited to, surface topography, historical data (e.g., historical data stored in a memory), or the like.

The determination that a first cluster of points at a first time is related to a second cluster of points at a second time, at step 350 of the process illustrated in FIG. 3, may be made based on determining if the distance between the first cluster of points and the second cluster of points is within the propagation threshold. The distance between the first cluster of points and the second cluster of points may be measured from a first point within the area occupied by the first cluster of points and a second point within the area occupied by the second cluster of points.

According to an exemplary embodiment of the present invention, the first point and/or the second point may be the center of the first cluster of points and second cluster of points, respectively. The center of a cluster of points may be determined by averaging the physical location of each point within the cluster of points such. For example, a cluster of points may have three points and each of the three points may have a respective X, Y, and Z coordinate. The coordinates for the first point may be X1, Y1, and Z1, for the second point may be X2, Y2, and Z2, and for the third point may be X3, Y3, and Z3. The center of the cluster of points may be determined by ((X1+X2+X3/3), (Y1+Y2+Y3/3), (Z1+Z2+Z3/3).

According to another exemplary embodiment of the present invention, the first point and/or the second point may be determined by assigning weights to one or more points within a cluster of points. For example, one or more weights may be assigned to one or more points within a cluster of points based on the voltage corresponding to each point. A point within the cluster of points may be weighted higher based on exhibiting a higher relative voltage and, similarly, a point within the cluster of points may be weighted lower based on exhibiting a lower relative voltage. The weights determined based on voltage may be relative to a predetermined voltage or based on a dynamically determined voltage based on the different voltage values of each of the points within a cluster of points.

The relation between a first cluster of points at a first time and a second cluster of points at a second, subsequent, time may indicate that the electrical activity within an intra-body organ propagates from the first cluster of points to the second cluster of points.

At step 360 of the process illustrated in FIG. 3, a visual indication for one or more propagation routes from a first cluster of points, at a first time, to a related second cluster of points, at a second time, may be provided. The visual indication may be any applicable visual indications such as an arrow, a highlighting of points within clusters of points, changes in color or pattern, or the like. The visual indication may identify the propagation route of electrical activity within an intra-body organ such that the visual indication identifies the direction and distance of the change in electrical activity.

Figure 4A:
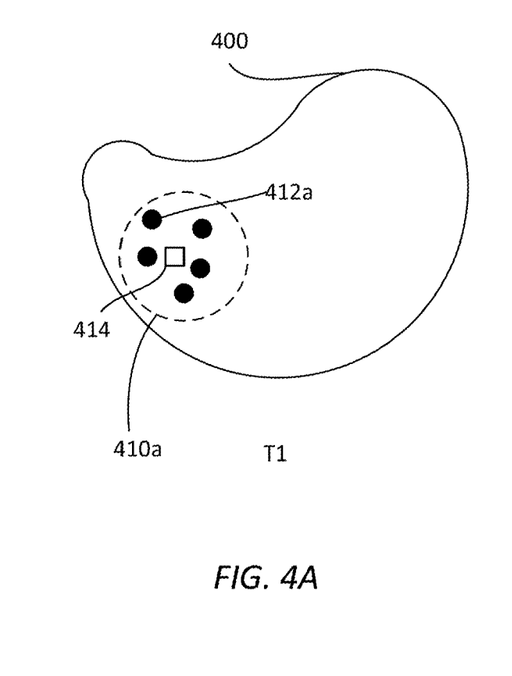
FIG. 4A is a diagram of an intrabody organ at a first time.
Figure 4B:
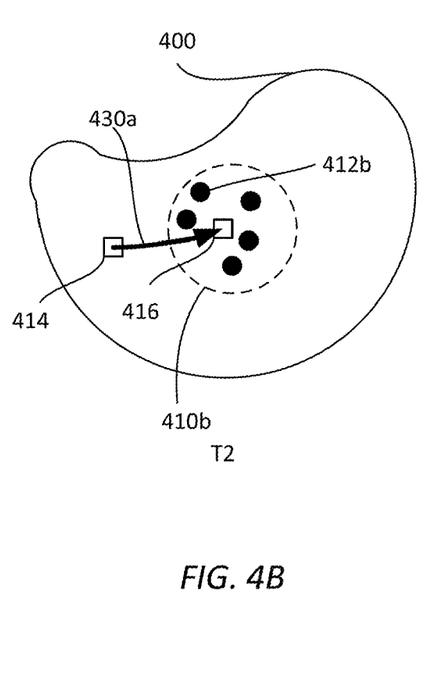
FIG. 4B is a diagram of the intrabody organ of FIG. 4A at a second time.
Figure 4C:
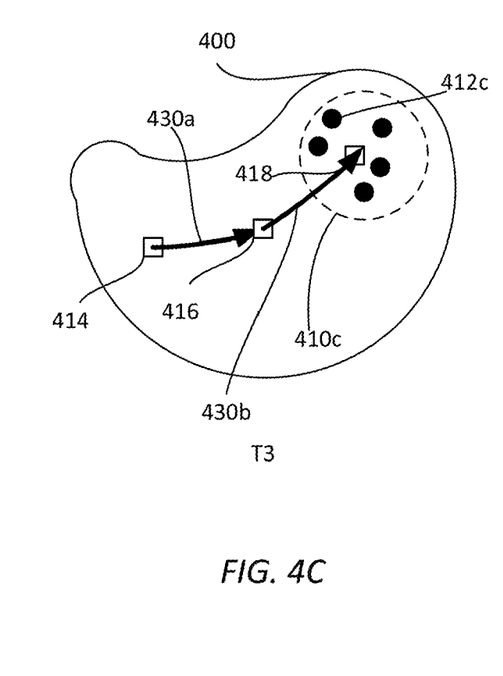
FIG. 4C is a diagram of the intrabody organ of FIG. 4A at a third time.

FIG. 4A, FIG. 4B, and FIG. 4C show an intrabody organ 400 with a first cluster of points 410a at a first time T1, a second related cluster of points 410b at a second time T2, and a related third cluster of points 410c at a third time T3, respectively. Each cluster of points includes active points 412a, 412b, and 412c, respectively in FIG. 4A, FIG. 4B, and FIG. 4C. It will be noted that inactive points on the surface of intrabody organ 400 are not shown for simplicity. The first cluster of points 410a includes active points that are each within a threshold proximity of at least one other active point within the first cluster of points 410a. Similarly, the second cluster of points 410b and third cluster of points 410c includes active points that are each within a threshold proximity of at least one other active point within the respective second cluster of points 410b and third cluster of points 410c.

As shown in FIG. 4A, a center point 414 is the center of the first cluster of points 410a. As shown in FIG. 4B, a center point 416 is the center of the second cluster of points 410b. As shown in FIG. 4C, a center point 418 is the center of the third cluster of points 410c. The three clusters of points 410a, 410b, and 410c of FIG. 4A, FIG. 4B, and FIG. 4C may be related such that the first cluster of points 410a and the second cluster of points 410b may be within a propagation threshold of each other and such that the second cluster of points 410b and the third cluster of points 410c are within the propagation threshold of each other. For example, the propagation threshold may be based on a propagation velocity of 4 μm/millisecond, the time duration between T1 and T2 may be 2 milliseconds, and the time duration between T2 and T3 may be 3 milliseconds. Accordingly, the propagation threshold between the first cluster of points 410a at time T1 and the second cluster of points 410b at time T2 may be 8 μm (i.e., 2 milliseconds multiplied (T2−T1) by the propagation velocity of 4 μm/millisecond) and the propagation threshold between the second cluster of points 410b at time T1 and the third cluster of points 410c at time T3 may be 12 μm (i.e., 3 milliseconds multiplied (T2−T1) by the propagation velocity of 4 μm/millisecond). According to the example shown in FIG. 4A, FIG. 4B, and FIG. 4C, the center 416 of the second cluster of points 410b may be within 8 μm of the center 414 of the first cluster of points 410a and, thus, the first cluster of points 410a and the second cluster of points 410b may be related. Similarly, the center 418 of the third cluster of points 410c may be within 12 μm of the center 416 of the second cluster of points 410b and, thus, the second cluster of points 410b and the third cluster of points 410c may be related. According to an exemplary embodiment of the present invention, the third cluster of points may also be related to the first cluster of points based on the common relation of both the first and third cluster of points with the second cluster of points.

As shown in FIG. 4B, visual indication 430a is provided from the center 414 of the first cluster of points 410a to the center 416 of the second cluster of points 410b. Notably, the visual indication 430a is provided based on the determination that the first cluster of points 410a and the second cluster of points 410b are related. Similarly, as shown in FIG. 4C visual indication 430b is provided from the center 416 of the second cluster of points 410b to the center 418 of the third cluster of points 410c. Notably, the visual indication 430b is provided based on the determination that the second cluster of points 410b and the third cluster of points 410c are related. According to an embodiment, the centers 414, 416, and 418 shown in FIG. 4A, FIG. 4B, and FIG. 4C may not be rendered on a display and may instead be used to determine the location of visual indications such as visual indication 430a and/or visual indication 430b.

According to an exemplary embodiment of the present invention, a cluster of points may be determined to be unrelated to a previously identified cluster of points. For example, a first cluster of points may be identified at a first time and a second cluster of points may be identified at a second time. However, the second cluster of points may have a center point that is at a distance that is greater than a propagation threshold distance. Accordingly, the first cluster of points and the second cluster of points may not be determined to be related such that no visual indication for a propagation route is provided from the first cluster of points to the second cluster of points.

Figure 5A:
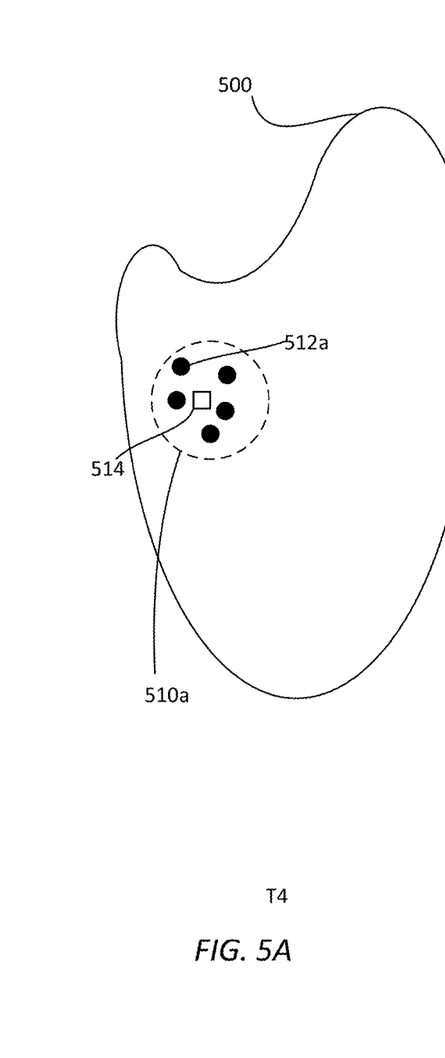
FIG. 5A is a diagram of another intrabody organ at a first time.
Figure 5B:
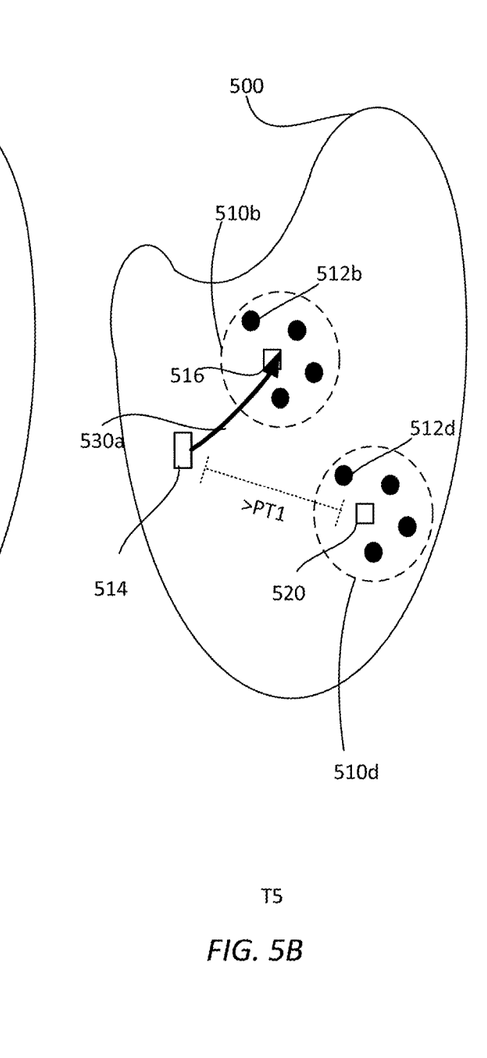
FIG. 5B is a diagram of the intrabody organ of FIG. 5A at a second time.
Figure 5C:
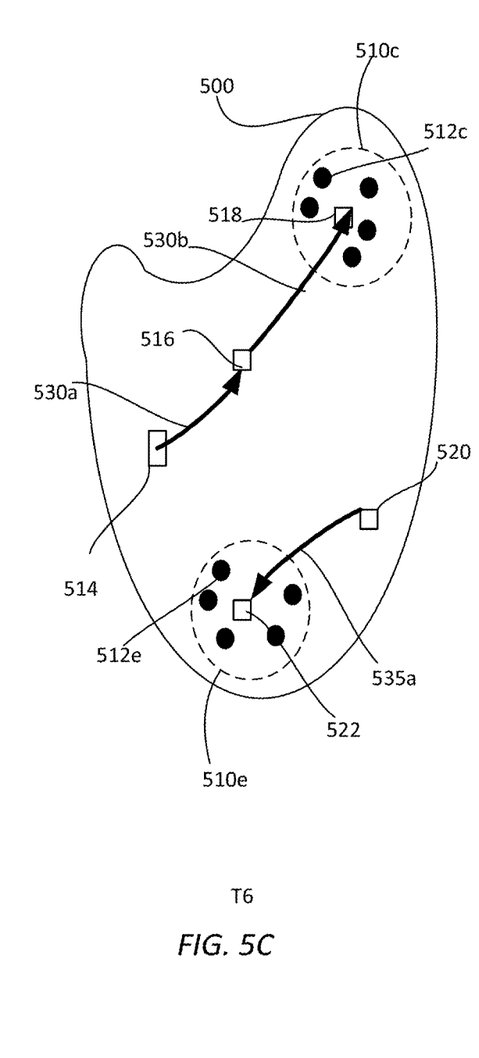
FIG. 5C is a diagram of the intrabody organ of FIG. 5A at a third time.

To clarify, two unrelated clusters of points at two different times may correspond to unrelated electrical activity. FIG. 5A, FIG. 5B, and FIG. 5C include an example of unrelated clusters of points such that unrelated electrical activity may be present within the intra-body organ.

FIG. 5A, FIG. 5B, and FIG. 5C show an intrabody organ 500 with a first cluster of points 510a at a first time T4, a related second cluster of points 510b (i.e., related to the first cluster of points 510a) and an unrelated third cluster of points 510d (i.e., unrelated to the first cluster of points 510a) at a second time T5, a related fourth cluster of points 510c (i.e., related to the second cluster of points 510b) and a related fifth cluster of points 510e (i.e., related to the third cluster of points 510d) at a third time T6 respectively. Each cluster of points includes active points 512a, 512b, 512c, 512d, and/or 512e. It will be noted that inactive points on the surface of intrabody organ 500 are not shown for simplicity. Each cluster of points shown in FIG. 5A, FIG. 5B, and FIG. 5C includes active points that are each within a threshold proximity of at least one other active point within the respective cluster of points.

As shown in FIG. 5A, a center point 514 is the center of the first cluster of points 510a. As shown in FIG. 5B, a center point 516 is the center of the second cluster of points 510b and a center point 520 is the center of the third cluster of points 510c. As shown in FIG. 5C, a center point 518 is the center of the fourth cluster of points 510c and a center point 522. Notably, the first cluster of points 510a, at the first time T4 and the third cluster of points 510d at the second time T5 may not be related. For example, the third cluster of points 510d may be greater than a propagation threshold away from the first cluster of points 510a, as indicated by the distance>PT1 in FIG. 5B. For example, the propagation threshold may be based on a propagation velocity of 4 μm/millisecond, the time duration between T4 and T5 may be 2 milliseconds, resulting in a propagation threshold of 8 μm between T4 and T5. The center 520 of the third cluster of points 510d may be greater than 8 μm (e.g., 9 μm) away from the center 514 of the first cluster of points 510a, such that the first cluster of points 510a and the third cluster of points 510d may not be related.

The clusters of points 510a, 510b, and 510c of FIG. 5A, FIG. 5B, and FIG. 5C may be related such that the first cluster of points 510a and the second cluster of points 510b may be within a propagation threshold of each other and such that the second cluster of points 510b and the fourth cluster of points 510c are within the propagation threshold of each other, as described in relation to FIG. 4A, FIG. 4B, and FIG. 4C. Additionally, the clusters of points 510d and 510e may be related such that the third cluster of points 510d and the fifth cluster of points 510e may be within a propagation threshold of each other. For example, the propagation threshold may be based on a propagation velocity of 4 μm/millisecond, the time duration between T5 and T6 may be 3 milliseconds (i.e., resulting in a propagation threshold of 12 μm from T5 to T6. Accordingly, the center 520 of the third cluster of points 510d at the second time T5 may be within 12 μm from the center 522 of the fifth cluster of points 510e at the third time T6, resulting in the third cluster of points 510d and the fifth cluster of points 510e being related.

As shown in FIG. 5B, visual indication 530a is provided from the center 514 of the first cluster of points 510a to the center 516 of the second cluster of points 510b. Notably, there is no visual indication provided between the first cluster of points 510a and the third cluster of points 510d because, as disclosed herein, the first cluster of points 510a and the third cluster of points 510d are not related (e.g., the distance between the two clusters exceeds a propagation threshold). As shown in FIG. 5C visual indication 530b is provided from the center 516 of the second cluster of points 510b to the center 518 of the fourth cluster of points 510c. Additionally, a visual indication 535a is provided from the center 520 if the third cluster of points 510d to the center 522 of the fifth cluster of points 510e, based on the third cluster of points 510d and the fifth cluster of points 510e being related. It should be noted that the direction of the visual indication 535a is in a different direction than the visual indications 530a and 530b as different areas of an intrabody organ may experience electrical activity and propagation differently. In the example shown in FIG. 5A, FIG. 5B, and FIG. 5C, visual indications 530a and 530b show a first propagation route of electrical activity and visual indication 535a shows a different second propagation route of electrical activity.

Although FIG. 5A, FIG. 5B, and FIG. 5C shows two unrelated first cluster of points 510a and third cluster of points 510c, it will be noted that, according to an exemplary embodiment of the present invention, two or more propagation routes may initiate from a common cluster of points. As an example, a first cluster of points at a first time may be related to two different clusters of points at a second time. Accordingly, two different propagation routes may extend from the first cluster of points (i.e., one each to each of the two related clusters of points). Each individual propagation route may be identified by respective visual indicators and may remain independent of the other propagation route.

Figure 5D:
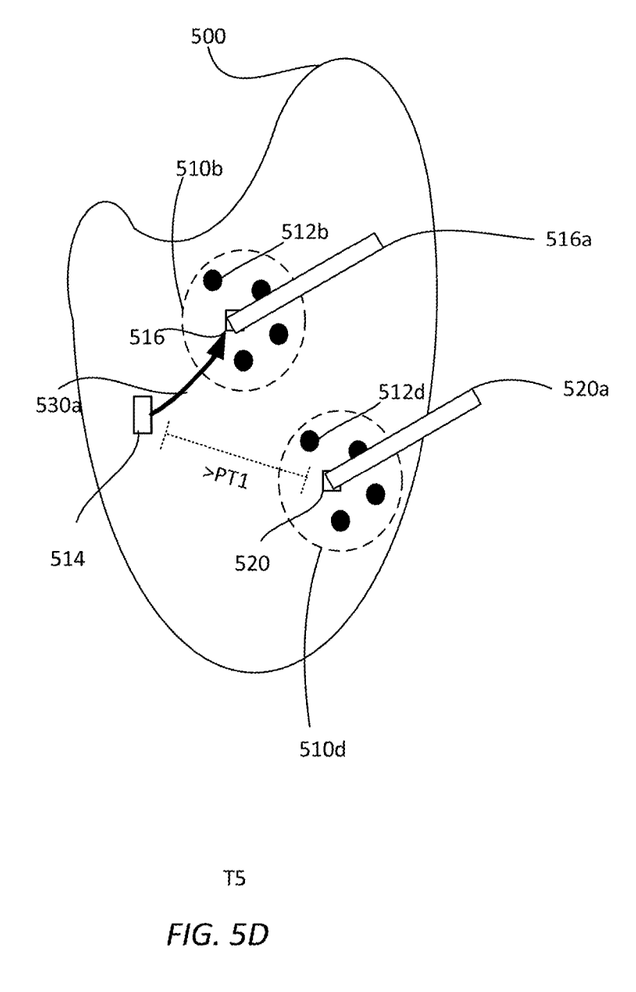
FIG. 5D is a diagram of the intrabody organ of FIG. 5a at a second time and with ripple electrical activity indications.

According to an exemplary embodiment of the present invention, as shown in FIG. 5D, a three-dimensional or pseudo three-dimensional indication of electrical activity at a cluster of points maybe provided. FIG. 5D is the same view of the intra-body organ 500 at a second time T5 that includes a related second cluster of points 510b (i.e., related to the first cluster of points 510a) and an unrelated third cluster of points 510d (i.e., unrelated to the first cluster of points 510a), as shown in FIG. 5B. FIG. 5D also includes a first bar 516a and a second bar 520a which are indications of electrical activity at the second cluster of points 510b and third cluster of points 510d respectively. Notably, an indication, such as a three-dimensional or pseudo three-dimensional bar may be provided via a display to indicate a cluster of points (e.g., a center of a cluster of points) that exceed an activity threshold, as disclosed herein. Such an indication may be provided at different times based on the respective clusters of points at that time. As an example, over the span of three different times where at least one cluster of points with electrical activity that exceeds an activity threshold is provided, there may be at least three different indications (e.g., three dimensional bars) originating from the center of each respective cluster of points. Such indications may be present during the span of the electrical activity exceeding an activity threshold for a given cluster of points such that a given indication is no longer provided once the electrical activity is no longer present at a given location.

Figure 6A:
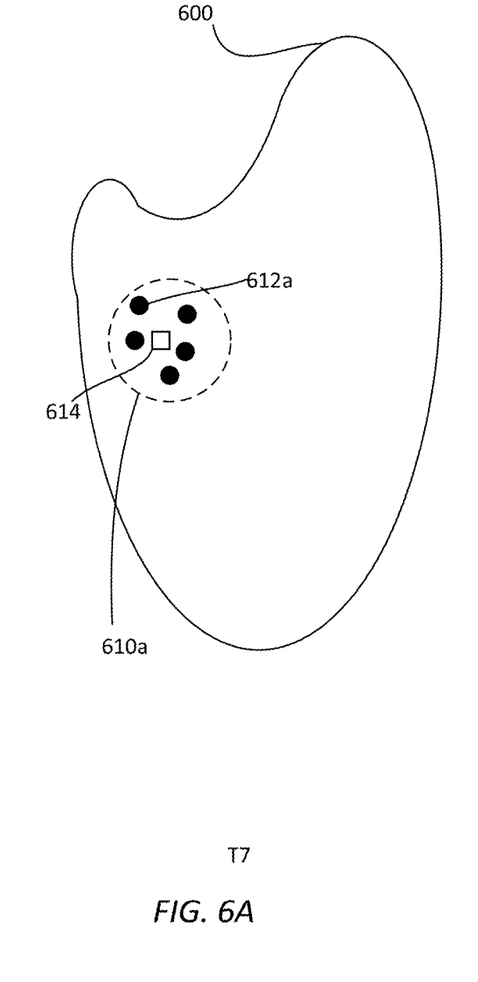
FIG. 6A is a diagram of another intrabody organ at a first time.
Figure 6B:
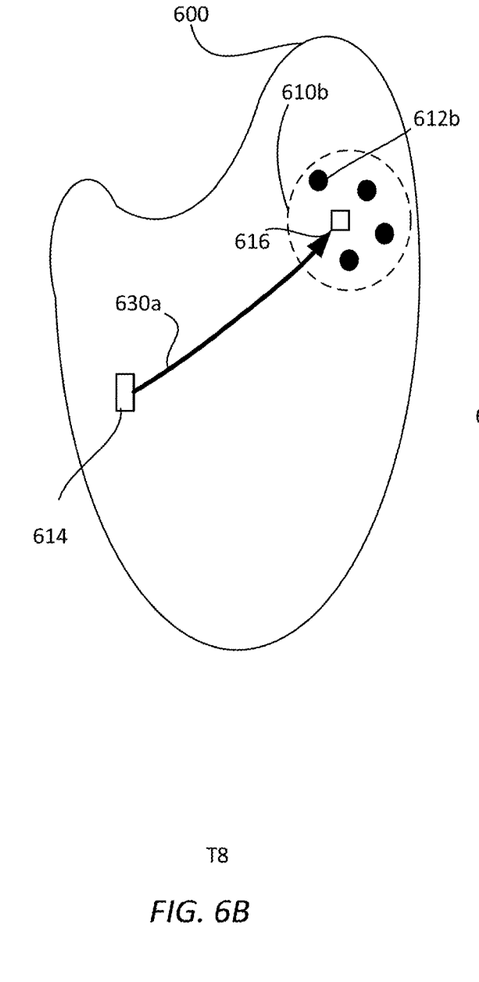
FIG. 6B is a diagram of the intrabody organ of FIG. 6A at a second time.
Figure 6C:
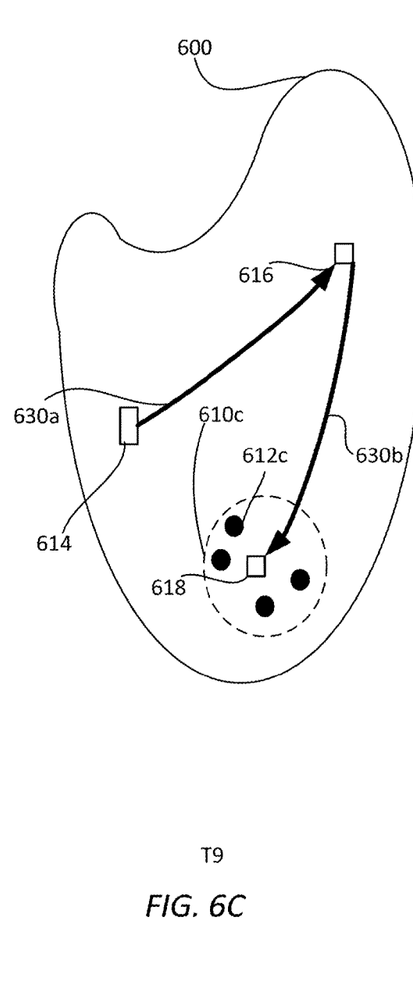
FIG. 6C is a diagram of the intrabody organ of FIG. 6A at a third time.

According to an exemplary embodiment of the present invention, one or more patterns may be identified from one or more propagation routes. Such patterns may be visually provided via the visual indications, as disclosed herein. Further, an identified pattern may be provided to a medical professional through an alert or may otherwise be stored in a memory. For example, FIG. 6A, FIG. 6B, and FIG. 6C show an intrabody organ 600 with a first cluster of points 610a at a first time T7, a related second cluster of points 610b, and at a second time T8, a related third cluster of points 610c at a third time T9. Each cluster of points includes active points 612a, 612b, and 612c. It will be noted that inactive points on the surface of intra-body organ 600 are not shown for simplicity. Each cluster of points shown in FIG. 6A, FIG. 6B, and FIG. 6C includes active points that are each within a threshold proximity of at least one other active point within the respective cluster of points.

As shown in FIG. 6A, a center point 614 is the center of the first cluster of points 610a. As shown in FIG. 6B, a center point 616 is the center of the second cluster of points 610b. As shown in FIG. 6C, a center point 618 is the center of the third cluster of points 610c. The three clusters of points 610a, 610b, and 610c of FIG. 6A, FIG. 6B, and FIG. 6C may be related such that the first cluster of points 610a and the second cluster of points 610b may be within a propagation threshold of each other and such that the second cluster of points 610b and the third cluster of points 610c are within the propagation threshold of each other.

As shown in FIG. 6B, a visual indication 630a may be provided from the center 614 of the first cluster of points 610a to the center 616 of the second cluster of points 610b. Additionally, as shown in FIG. 6C, a visual indication 630b may be provided from the center 616 of the second cluster of points 610b to the center 618 of the third cluster of points 610c. As shown in FIG. 6C the propagation route indicated by the visual indications 630a and 630b create a rotor pattern such that the propagation of electrical activity changes direction back towards the first cluster of points 610a at the third time T9. A propagation route pattern (e.g., a rotor pattern) may be identified based on one or more criteria such as a shape, an overlap, a direction, or the like. Alternatively, a propagation route pattern may be identified based on comparing a determined propagation route (e.g., the visual indications 630*a* and 630*b*) to stored propagation route patterns (e.g., stored in a memory such as memory 42 of FIG. 1). An identified propagation route pattern may be stored in memory (e.g., memory 42) and/or may be provided to a medical professional via a visual alert (e.g., on a local or remote display, on a mobile device, etc.), an audible alert, a vibration, or the like.

Any of the functions and methods described herein can be implemented in a general-purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer-readable media). The results of such processing can be maskworks that are then used in a semiconductor manufacturing process to manufacture a processor which implements features of the disclosure.

Any of the functions and methods described herein can be implemented in a computer program, software, or firmware incorporated in a non-transitory computer-readable storage medium for execution by a general-purpose computer or a processor. Examples of non-transitory computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

It should be understood that many variations are possible based on the disclosure herein. Although features and elements are described above in particular combinations, each feature or element can be used alone without the other features and elements or in various combinations with or without other features and elements.

The invention claimed is:

1. A method for improving intra-body visualization, the method comprising:
sending, via at least one electrode, at least one electrical signal;
receiving first electrical activity at a first time for a plurality of points on an intra-body surface, based on movement of the at least one electrical signal through the intra-body surface;
identifying a first cluster of points from the plurality of points, based on the first electrical activity, the first cluster of points each exhibiting electrical activity above an activity threshold;
sending, via the at least one electrode, at least one second electrical signal;
receiving second electrical activity at a second time in a second location for the plurality of points on the intra-body surface, based on movement of the at least one second electrical signal through the intra-body surface;
identifying a second cluster of points from the plurality of points, based on the second electrical activity, the second cluster of points each exhibiting electrical activity above the activity threshold;
determining that the first cluster of points and the second cluster of points are related based on a propagation threshold distance; and
providing a first visual indication for a first propagation route from the first cluster of points to the second cluster of points based on determining that they are related, wherein
the first visual indication is mapping created from at least the first electrical activity and the second electrical activity,
the propagation threshold distance is a distance based on a propagation velocity between at least the first electrical activity at the first cluster of points and the second electrical activity at the second cluster of points multiplied by a difference between the first time and the second time,
on a condition that a distance between the first cluster of points and the second cluster of points is greater than the propagation threshold distance, the first cluster of points and the second cluster of points are not related, and
on a condition that the distance between the first cluster of points and the second cluster of points is less than or equal to the propagation threshold distance, the first cluster of points and the second cluster of points are related.

2. The method of claim 1, wherein identifying the first cluster of points is based on a proximity of a first point of the plurality of points to a second point of the plurality of points being within a threshold proximity.

3. The method of claim 2, wherein identifying the first cluster of points is further based on identifying an outlier point that is over the threshold proximity from the first point and the second point such that the outlier point is excluded from the first cluster of points.

4. The method of claim 1, further comprising displaying the first visual indication of the first propagation route.

5. The method of claim 1, wherein the first visual indication of the first propagation route is an arrow starting at the first cluster of points and ending at the second cluster of points.

6. The method of claim 1, further comprising:
sending, via the at least one electrode, at least one third electrical signal;
receiving third electrical activity at a third time for the plurality of points on an intra-body surface, based on movement of the at least one third electrical signal through the intra-body surface;
identifying a third cluster of points from the plurality of points, the third cluster of points each exhibiting electrical activity above the activity threshold;
determining that the second cluster of points and the third cluster of points are related based on the propagation threshold distance; and
providing a second visual indication of a second propagation route from the second cluster of points to the third cluster of points based on determining that the second cluster of points and the third cluster of points are related.

7. The method of claim 6, further comprising determining a rotor pattern based on first propagation route and the second propagation route.

8. The method of claim 1, further comprising:
sending, via the at least one electrode, at least one third electrical signal;
receiving third electrical activity at a third time for the plurality of points on an intra-body surface, based on movement of the at least one third electrical signal through the intra-body surface;
identifying a third cluster of points from the plurality of points, the third cluster of points each exhibiting electrical activity above the activity threshold;
determining that the first cluster of points and the third cluster of points are related based on the propagation threshold distance; and
providing a second visual indication of a second propagation route from the first cluster of points to the third cluster of points based on determining that the first cluster of points and the third cluster of points are related.

9. The method of claim 8, further comprising displaying the first visual indication of the first propagation route and the second visual indication of the second propagation route.

10. A system for improving intra-body visualization, the system comprising: a probe configured to:
send at least one first electrical signal and at least one second electrical signal;
sense first electrical activity at a first time for a plurality of points on an intra-body surface, based on movement of the at least one electrical signal through the intra-body surface and second electrical activity at a second time for the plurality of points, based on movement of the at least one second electrical signal through the intra-body surface;
a processor configured to;
identify a first cluster of points from the plurality of points, the first cluster of points each exhibiting electrical activity above an activity threshold;
identify a second cluster of points from the plurality of points, the second cluster of points each exhibiting electrical activity above the activity threshold;
determine that the first cluster of points and the second cluster of points are related based on a propagation threshold distance; and
provide a first visual indication of a first propagation route from the first cluster of points to the second cluster of points based on determining that they are related, wherein
the first visual indication is mapping created from at least the first electrical activity and the second electrical activity,
the propagation threshold distance is a distance based on a propagation velocity between at least the first electrical activity at the first cluster of points and the second electrical activity at the second cluster of points multiplied by a difference between the first time and the second time,
on a condition that a distance between the first cluster of points and the second cluster of points is greater than the propagation threshold distance, the first cluster of points and the second cluster of points are not related, and
on a condition that the distance between the first cluster of points and the second cluster of points is less than or equal to the propagation threshold distance, the first cluster of points and the second cluster of points are related.

11. The system of claim 10, wherein identifying the first cluster of points is based on a proximity of the points in the first cluster of points to each other.

12. The system of claim 11, wherein identifying the first cluster is further is based on identifying an outlier point that is over a threshold distance from the first cluster of points.

13. The system of claim 10, further comprising a display configured to render the first visual indication of the first propagation route.

14. The system of claim 10, wherein the first visual indication of the first propagation route is an arrow starting at a center of the first cluster and ending at a center of the second cluster.

15. The system of claim 10, wherein the probe is further configured to send at least one third electrical signal and sense third electrical activity at a third time for the plurality of points on the intra-body surface, based on movement of the at least one third electrical signal through the intra-body surface and the processor is further configured to:
identify a third cluster of points from the plurality of points, the third cluster of points each exhibiting electrical activity above the activity threshold;
determine that the second cluster of points and the third cluster of points are related based on the propagation threshold distance; and
provide a second visual indication of a second propagation route from the second cluster of points to the third cluster of points based on determining that the second cluster of points and the third cluster of points are related.

16. The system of claim 15, wherein the processor is further configured to determine a rotor pattern based on identifying a circular pattern exhibited by locations of first cluster of points, second cluster of points, and third cluster of points.

17. The system of claim 10, wherein the probe is further configured send at least one third electrical signal and sense third electrical activity at a third time for the plurality of points on the intra-body surface, based on movement of the at least one third electrical signal through the intra-body surface and the processor is further configured to:
identify a third cluster of points from the plurality of points, the third cluster of points each exhibiting electrical activity above the activity threshold;
determine that the first cluster of points and the third cluster of points are related based on the propagation threshold distance; and
provide a second visual indication of a second propagation route from the first cluster of points to the third cluster of points based on determining that the first cluster of points and the third cluster of points are related.

18. The system of claim 17, further comprising a display configured to render the first visual indication of the first propagation route and the second visual indication of the second propagating route.

* * * * *

UNITED STATES PATENT AND TRADEMARK OFFICE
CERTIFICATE OF CORRECTION

PATENT NO. : 11,607,272 B2
APPLICATION NO. : 16/681411
DATED : March 21, 2023
INVENTOR(S) : Natan Sharon Katz et al.

It is certified that error appears in the above-identified patent and that said Letters Patent is hereby corrected as shown below:

In the Specification

In Column 1, Line 55, delete "disclosure" and insert -- disclosed --, therefor.

In Column 2, Line 63, delete "disclosure" and insert -- disclosed --, therefor.

In Column 4, Line 66, delete "server" and insert -- server by --, therefor.

In Column 4, Line 67, delete "@)." and insert -- ®). --, therefor.

In Column 6, Line 30, delete "a" and insert -- have a --, therefor.

In Column 8, Line 55, delete "points such." and insert -- points. --, therefor.

In Column 8, Line 61, delete "((X1" and insert -- (X1 --, therefor.

In Column 11, Line 26, delete "(i.e.," and insert -- i.e., --, therefor.

In Column 12, Line 4, delete "maybe" and insert -- may be --, therefor.

In the Claims

In Column 15, Line 23, in Claim 10, delete "a probe configured to:" and insert the same on Line 24, as new sub-point.

In Column 15, Line 33, in Claim 10, delete "to;" and insert -- to: --, therefor.

In Column 16, Line 8, in Claim 12, delete "further is" and insert -- further --, therefor.

Signed and Sealed this
Twelfth Day of September, 2023

Katherine Kelly Vidal
*Director of the United States Patent and Trademark Office*